(12) United States Patent
Bittner et al.

(10) Patent No.: US 6,193,129 B1
(45) Date of Patent: Feb. 27, 2001

(54) CUTTING BLADE FOR A SURGICAL ANASTOMOSIS STAPLING INSTRUMENT

(75) Inventors: John Raymond Bittner, Palmyra, VA (US); Aaron Christopher Voegele, Loveland; Dale Gene Boling, Georgetown, both of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/490,855

(22) Filed: Jan. 24, 2000

(51) Int. Cl.[7] ................................................ A61B 17/068
(52) U.S. Cl. ........................................ 227/180.1; 227/19
(58) Field of Search ................................. 227/19, 175.1, 227/176.1, 179.1, 180.1; 606/219

(56) References Cited

U.S. PATENT DOCUMENTS

| 4,207,898 | 6/1980 | Becht . | |
|---|---|---|---|
| 4,289,133 | 9/1981 | Rothfuss . | |
| 4,319,576 | 3/1982 | Rothfuss . | |
| 4,893,622 | * 1/1990 | Green et al. | 227/180.1 |
| 5,163,943 | * 11/1992 | Mohiuddin et al. | 227/180.1 |
| 5,271,544 | * 12/1993 | Fox et al. | 227/19 |
| 5,639,008 | * 6/1997 | Gallagher et al. | 227/175.1 |
| 5,860,581 | * 1/1999 | Robertson et al. | 227/180.1 |

* cited by examiner

*Primary Examiner*—Scott A. Smith
(74) *Attorney, Agent, or Firm*—Louis J. Capezzuto (57) ABSTRACT

A surgical cutting and stapling instrument has an improved blade. The surgical instrument has a handle with a moveable firing trigger, a shaft extending from the handle, and a stapling head at the end of the shaft. An array of staples are located within the stapling head. An anvil is coupled to the stapling head and has staple forming pockets facing and in alignment with the staples. A breakaway washer is located within the anvil assembly and has a pair of parallel spaced walls with a thin web extending therebetween. The thin web faces the distal face of the stapling head. A blade is located within the distal face of the stapling head and has a distal cutting edge and at least one wedge spike facing the annular thin web of the breakaway washer. When the anvil is moved adjacent to the stapling head and the firing trigger is closed, the staples are formed and the blade is moved to sever the breakaway washer in a two step process. First, the wedge spike of the blade penetrates the thin web of the breakaway washer and weakens the thin web by propagating a crack within the thin web. Second, once the breakaway washer is cracked, the distal cutting edge of the blade severs the thin web.

9 Claims, 9 Drawing Sheets

CUTTING BLADE FOR A SURGICAL ANASTOMOSIS STAPLING INSTRUMENT

FIELD OF THE INVENTION

The present invention relates, in general, to surgical stapling instruments for applying surgical staples to tissue and, more particularly, to a circular surgical stapling instrument having an improved circular blade.

BACKGROUND OF THE INVENTION

Circular surgical staplers are well known in the surgical field for the ease with which the instrument performs a previously difficult anastomotic stapling operation—the hemostatic joining of two pieces of tubular tissue together with a ring of staples. Such an instrument is ideally suited for intestinal or bowel surgery, and an instrument of this type is the Endopath™ ILS Endoscopic Curved Intraluminal Stapler manufactured by Ethicon Endo-Surgery, Cincinnati, Ohio. The circular stapling instrument has a distal stapling head that is available in a variety of sizes to match the organ size of the patient.

Circular stapling instruments are best known for their ability to anastomose or attach two pieces of intestinal or bowel tissue together in an end-to-end fashion. In general, staples are known to provide a good degree of hemostasis when applied to tubular tissue such as intestine or bowel. Circular stapling instruments hold a plurality of staples in an annular array of concentric rings within a body of the distal stapling head. A moveable anvil is used to compress or clamp the pieces of intestinal tissue together between the body and the anvil of the stapling head. A firing trigger is operatively coupled to the stapling head and actuation of the trigger ejects the annular array of staples from the body of the stapling head. The ejected staples pierce the clamped tissue and are formed into a ring of "B" shaped staples that securely join the pieces of intestinal tissue together. A circular blade or scalpel of generally cylindrical shape is located within the stapling head and is advanced distally to sever a small ring or "donut" of excess tissue from between the annular array of formed staples. Severing the donut of tissue opens a passageway between the joined pieces of intestinal tissue. The anastomosed tissue is released from the circular instrument by distally advancing the anvil away from the staple holder and drawing the anvil out through the passageway within the annular array of formed staples. Such a device was disclosed by Becht in U.S. Pat. No. 4,207,898 and by Rothfuss in U.S. Pat. No. 4,319,576.

One improvement to the circular stapler that has been well received by surgeons is the inclusion of a breakaway or backup washer within the anvil of the surgical stapler. The breakaway washer is an annular member of semi-rigid material located within the anvil in a location directly opposite to the circular blade. The annular ring has a pair of spaced annular walls joined together at the proximal end by a thin web of material. The thin web of material faces the circular blade and supports tissue as the circular blade is advanced. The advancing circular blade severs the clamped tissue and is slowed by contact with the thin web of the breakaway washer. A cutting edge of the circular blade is substantially parallel to the thin web of the breakaway washer such that the entire cutting edge contacts the thin web of the breakaway washer in a circular ring of contact. Continued application of force partially severs the thin web of material and the remaining thin web material abruptly breaks due to the applied pressure. As the breakaway washer breaks, the load or force required to advance the circular blade drops abruptly. This abrupt force change provides the surgeon with a clear tactile and an audible indication that the instrument has been fired. A circular stapling instrument having a breakaway or backup washer is taught in U.S. Pat. No. 4,289,133, by Rothfuss.

It is important to note that U.S. Pat. No. 4,289,133 discloses a circular blade having an annular cutting edge that is generally parallel to the thin web of the breakaway washer. The parallelism of the cutting edge to the thin web maximizes the contact area of the blade with the thin web and maximizes the input force required to sever the breakaway washer.

Whereas the breakaway washer was indeed a breakthrough device providing the surgeon with an audible and tactile indication that the anastomosis of the tubular organs is complete, the force required to sever or break the breakaway washer amounted to a large portion of the firing force of the instrument. The force required to break the breakaway washer rises to an abrupt peak over a narrow portion of the firing trigger stroke. An alternate embodiment of the circular blade disclosed in U.S. Pat. No. 4,289,133 is a circular blade having an undulating cutting edge. The undulating cutting edges has both peaks and valleys, and the peaks of the cutting edge contact and slices the breakaway washer before the valleys. The undulating cutting edge does not cut the entire thin web simultaneously and this distributes the cutting of the breakaway washer over a larger part of the firing stroke. This reduces the peak cutting forces, and the blade slices rather than penetrates or punches through the thin web.

Whereas the undulating cutting edge does indeed reduce the load or force to break the washer, it is accomplished by spreading the load over a larger portion of the firing stroke. Testing has indicated that an undulating cutting blade gradually slices the breakaway washer and does not provide the tactile and audible feeling that that is preferred by many surgeons.

Thus, an invention that reduces the peak firing force and provides a tactile and audible signal to the surgeon would be more acceptable. Presently, there is no known surgical anastomosis stapling instrument that can provide an improved interaction between the circular blade and the breakaway washer such that the surgeon is provided with both the desired tactile and audible feedback, and a reduction of the force needed to fire the instrument.

SUMMARY OF THE INVENTION

The present invention is a surgical cutting and stapling instrument for applying a plurality of staples to tissue. The surgical stapling instrument includes a handle portion and a firing trigger pivotably connected to the handle portion. A shaft extends from the handle portion and a stapling head is attached to the shaft. The stapling head has a distal face and an array of staple slots and staples located therein. The staples are operably coupled to the firing trigger. An anvil is coupled to the stapling head. The anvil has an array of staple forming pockets therein. The staple forming pockets are facing the distal face of the stapling head and are in alignment with the staple slots in the distal face for forming an array of the staples therebetween;

A breakaway washer is mounted within the anvil of the stapling head. The breakaway washer has a pair of parallel spaced walls and a thin web extending therebetween. The thin web faces the distal face of the stapling head.

A blade is located within the distal face of the stapling head and is operably coupled to the firing trigger. The blade has a distal cutting edge and at least one wedge spike protruding distally therefrom. The at least one wedge spike has a first and a second edge. The distal cutting edge and the at least one wedge spike face the annular thin web of the breakaway washer.

When the anvil is moved adjacent to the stapling head and the firing trigger is closed, the staples are formed and the blade is moved to sever breakaway washer. When the blade is moved, the at least one wedge spike of the blade penetrates the thin web of the breakaway washer and weakens the thin web by propagating at least one crack therein. The distal cutting edge of the blade severs the thin web having at least one crack therein.

That is, in a surgical procedure, the surgeon first clamps the surgical stapling and cutting instrument on tissue. Next, the surgeon fires the instrument is fired to form the staples in tissue. As the staples are formed, the wedge spikes of the blade penetrates the clamped tissue and the thin web of the breakaway washer. Lastly, the distal cutting edge of the blade severs the tissue and the breakaway washer.

Significantly, the novel blade of the surgical stapling and cutting instrument provides the surgeon with the desired tactile and audible feedback, and reduces the force to fire the instrument by reducing the force needed to sever the breakaway washer. Specifically, the novel blade of the present invention severs the breakaway washer in a novel two step process. First, the wedge spikes of the blade penetrate the thin web of the breakaway washer, and by wedging action, propagate at least one crack in the thin web of the breakaway washer away from the point of penetration. Second, the blade is advanced to contact and sever the weakened cracked thin web of the breakaway washer. Consequently, weakening the breakaway washer with at least one crack reduces the force to fire, and the desired tactile and audible feedback is obtained by severing the remaining uncracked portions of the thin web.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

The present invention is an improved surgical stapling instrument for applying surgical staples to tissue and, more particularly, to a circular surgical stapling instrument having an improved cutting blade. Circular stapling instruments having a circular cutting blade are well known in the art and described in the U.S. Pat. No. 4,319,576 (Rothfus), which is herein incorporated by reference.

Figure 1:
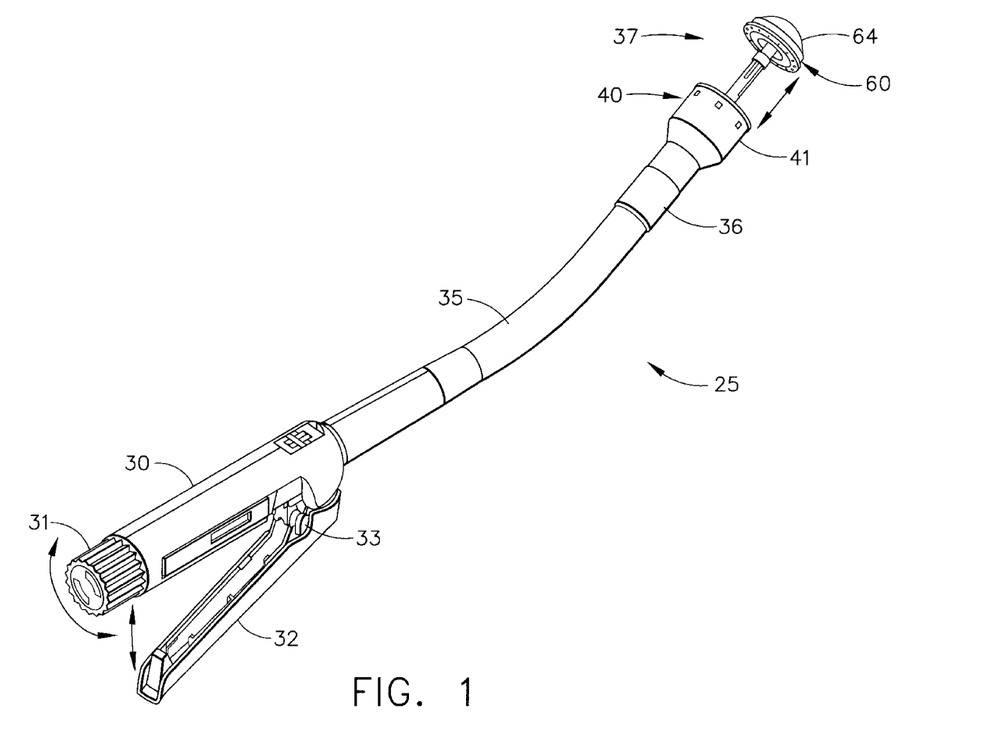
FIG. 1 is an isometric view of a surgical anastomosis stapling instrument.
Figure 5:
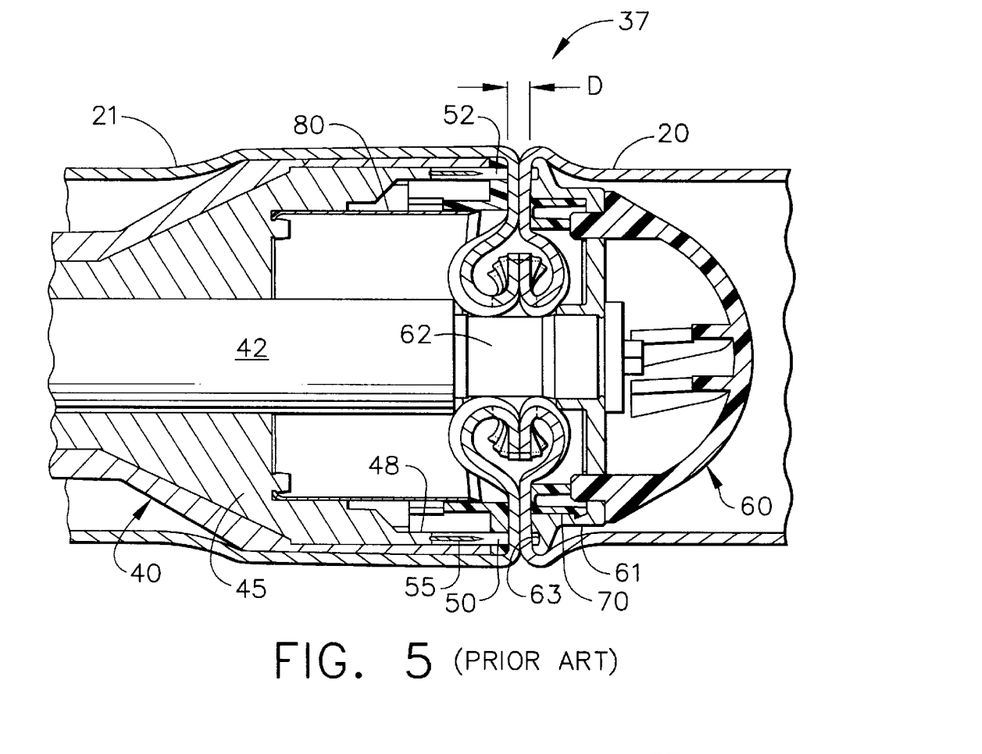
FIG. 5 is a side elevational view, in cross section, of FIG. 4 wherein the anvil assembly has been closed to a gap D.

Referring now to FIG. 1, a surgical stapling instrument 25 of the preferred invention has a handle 30 for the surgeon to grasp, a shaft 35 extending distally from the handle 30, and a distal stapling end effector 37 for the end-to-end anastomosis of cylindrical tissue. A moveable firing trigger 32 is pivotably connected to the handle 30. Firing trigger 32 is shown in the open position extending from the handle 30 and is moveable to a closed position adjacent to the handle 30. The shaft 35 is slightly curved for anatomical placement of the stapling end effector 37 into hard to reach lower anatomical positions. The stapling end effector 37 has a fixed stapling head assembly 40 and a movable anvil assembly 60 operably connected to an anvil closure knob 31. Rotation of the anvil closure knob 31 moves the anvil assembly 60 from the spaced away position shown in FIG. 1 to a position adjacent to the stapling head assembly (FIG. 5). The anvil assembly 60 is detachably connected to the stapling head assembly 40 and can be easily removed from the surgical stapling instrument 25 in the full open position. A firing trigger 32 is moveable from an open position to a closed position to staple and cut two sections of colon or bowel together within the stapling end effector 37. A safety latch 33 is shown in the locked position to lock the firing trigger 32 in the open position to prevent accidental firing. These operations will be described in greater detail below.

Figure 2:
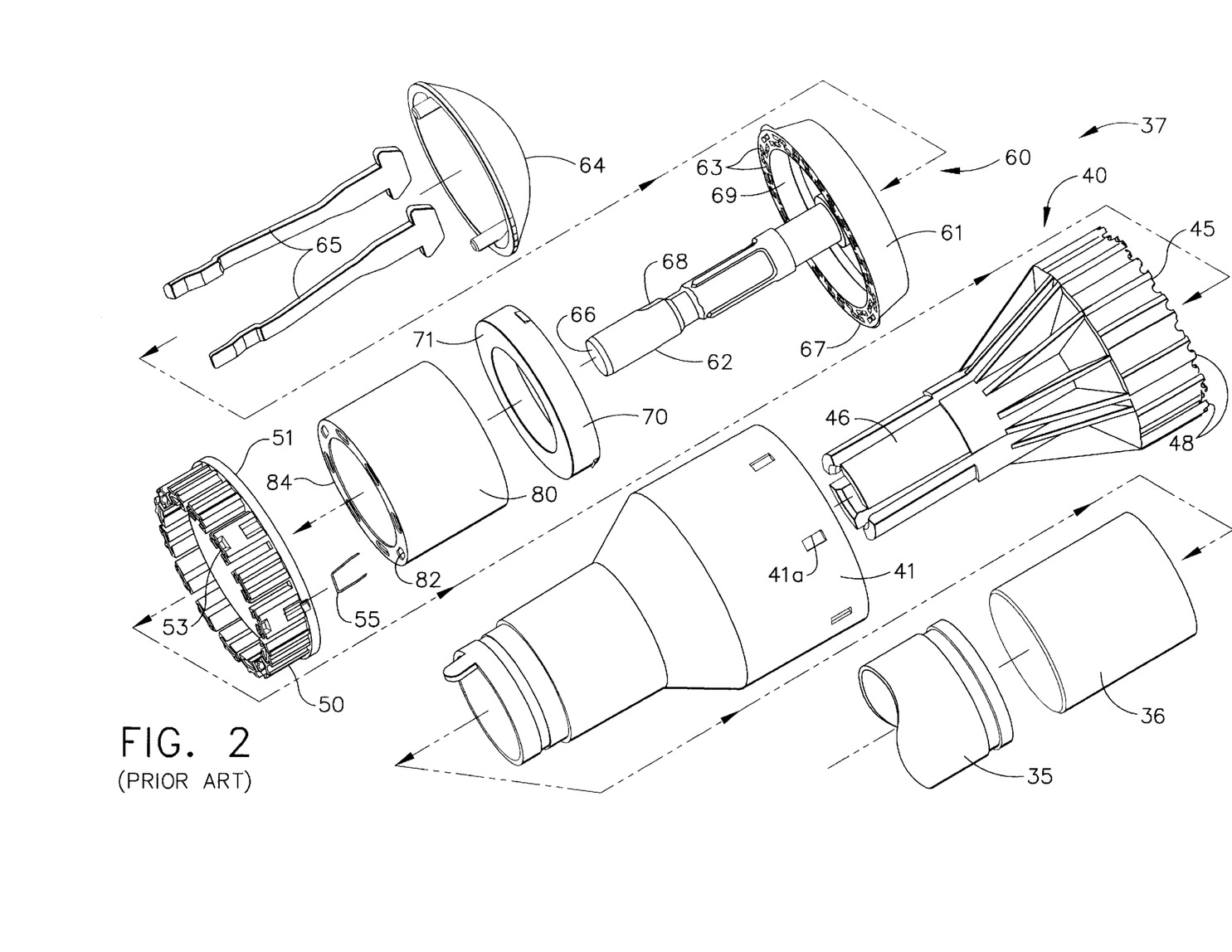
FIG. 2 is an exploded isometric view of the stapling end effector of the surgical anastomosis stapling instrument of FIG. 1 wherein the end effector has a prior art circular blade.

Referring now to FIG. 2, the elements that make up the anvil assembly 60 and the stapling head assembly 40 of the stapling end effector 37 are shown in exploded form. The stapling head assembly 40 has a hollow tubular casing 41 that is fixedly attached at the proximal end to the shaft 35 by a swaged ferrule 36. The casing 41 is funnel shaped and is open at the distal end for the reception of a staple holder 50. A series of locking holes 41a are circumferentially located about the tubular casing 41 to cooperate with a like number of locking pins 53 that extend from the staple holder 50 to fix the staple holder 50 in the casing 41.

A funnel shaped staple driver 45 is slidably located within the assembled casing 41 and the staple holder 50 and operably connected to the firing trigger 32. Staple holder 50 has a distal face 51 and an annular array of staple slots 52 (FIG. 3) extending longitudinally therein. Staple driver 45 has a like number of driver fingers 48 extending that are slidably received in the proximal portion of the staple slots 52. A staple 55 is received in the distal portion of the staple slots 52 in contact with a distal end of the driver fingers 48.

Figure 3:
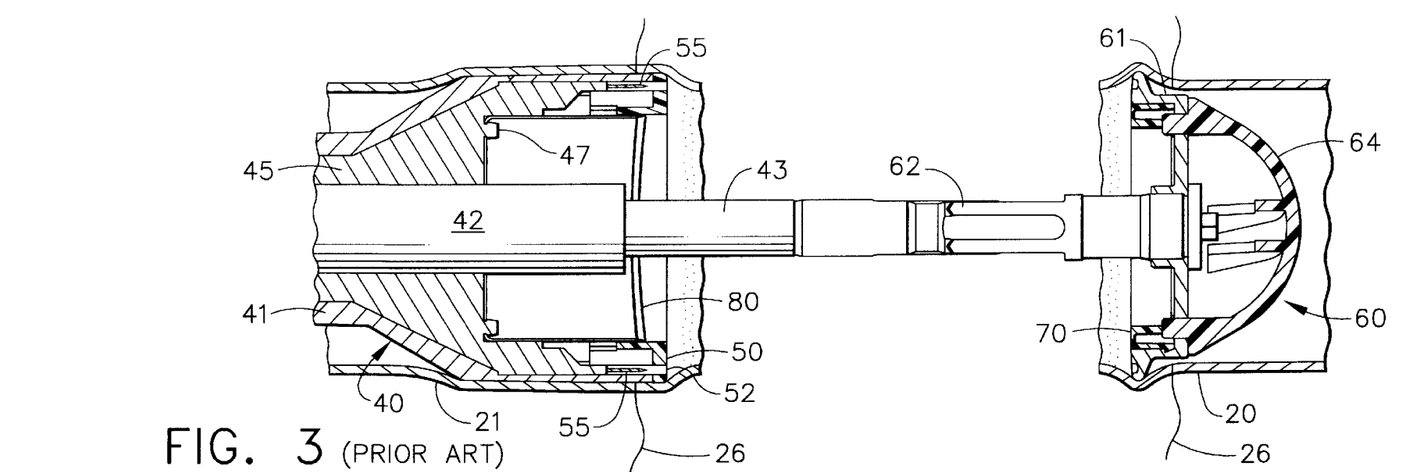
FIG. 3 is a side elevational view, in cross section, of the assembled stapling end effector of FIG.2 wherein the stapling head assembly is shown fully inserted into a section of purse string sutured inferior colon tissue and the anvil assembly is fully opened and inserted into a section of purse string sutured superior colon tissue.

The staple driver 45 is generally hollow and fixably receives a circular blade within the open distal end (FIG. 3). A prior art circular blade 80 is shown and described in FIGS. 2–7. As best shown in FIG. 7, the prior art circular blade 80 is a generally a hollow cylinder having a distal cutting edge 81, and a proximal blade base 84 having a central aperture 83. The cutting edge 81 of the prior art blade 80 is formed parallel to the blade base 84. A series of blade mounting holes 82 are equally spaced around the blade base 84 and fit over a like number of blade mounting pins 47 located within the staple driver 45. The circular blade 80 is attached to the staple driver 45 by swelling or staking the pins 47 (FIGS. 3–6) with the application of heat or ultrasonic energy (not shown).

Figure 4:
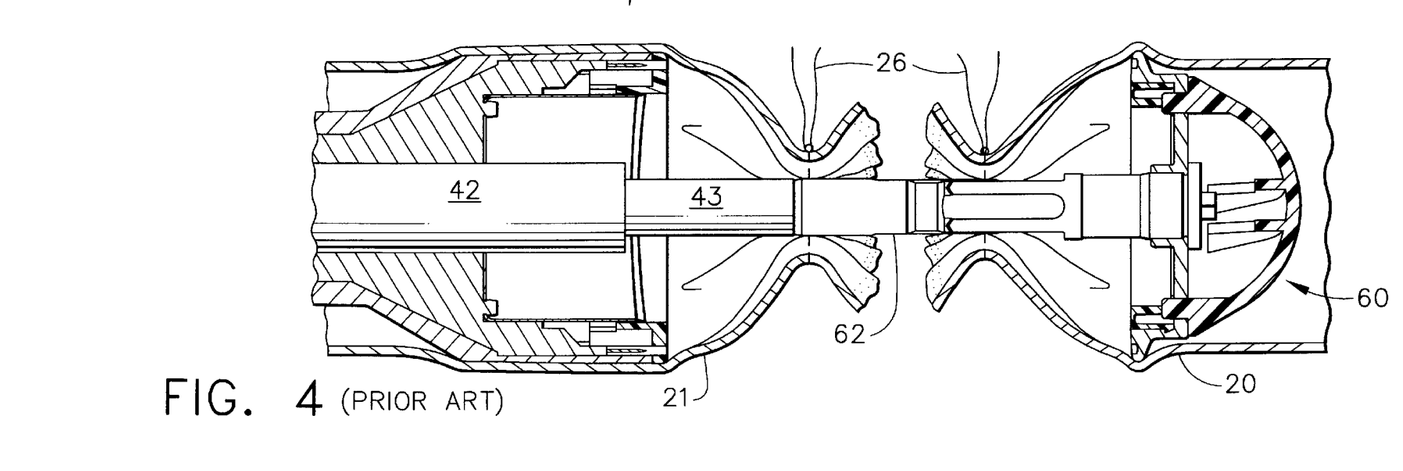
FIG. 4 is a side elevational view, in cross section, of FIG. 3 wherein the purse string sutures within the colon tissue are tightened and tied to draw the colon tissue tightly around the anvil shaft.

Anvil assembly 60 is shown in exploded form in FIG. 2 and removeably mounts to the stapling head assembly 40. The anvil assembly 60 has a disk shaped anvil 61 rigidly attached to a distal end of an anvil shaft 62. The anvil 61 has an outer ring 69 with an annular array of staple forming pockets 63 around the periphery of a proximal anvil face 67. An anvil shroud 64 is attached to the distal face of the anvil 61 to provide an atraumatic tip for the surgical stapling instrument 25. The anvil shaft 62 has a bore 66 therein and a pair of opposed clip slots 68 extend inwardly to communicate with the bore 66. A pair of flexible trocar clips 65 fixedly mount within the distal end of the bore 66 and extend outwardly into the clip slots 68. The clips 65 provide a detent for engaging a trocar 43 extending distally from the head assembly 40 (FIGS. 3 and 4). The detent operably connects the anvil assembly 60 to the anvil closure knob 31 (FIG. 1).

A breakaway washer 70 mounts within the outer end of the anvil assembly 60 and is fabricated or formed from a plastic material such as acrylonitrile butadiene styrene (ABS), polyethelene, polypropelene, polystyrene or any other semi-resilient engineering thermoplastic. The breakaway washer 70 is annular in shape and as shown the in cross section of FIG. 11, has an outer wall 71 and an inner wall 72 with a thin web 73 extending therebetween. The thin web 73 opposedly faces the distal cutting edge 81 of the circular blade 80 and is used as a backup surface for the tissue as it is being cut. The interaction of the breakaway washer 70 with circular blade 80 will be described in further detail below.

FIGS. 3–6 show how the surgical stapling instrument 25 is used to perform a double purse string suturing technique to anastomose two portions of colon tissue. For clarity, the stapling end effector 37 and colon tissue are shown in cross section to better illustrate the movement of the internal elements within the instrument 25 and the interaction of the instrument 25 with colon tissue. The anastomosis is performed with the prior art circular blade 80 so that the reader can understand the prior art and appreciate the improvements offered by the spiked circular blade 90 (FIG. 10) of the present invention. The spiked circular blade 90 will be described in greater detail later.

Prior to the view shown in FIG. 3, the sigmoid colon of a patient has been sectioned to excise a portion of cancerous tissue producing a section of superior colon tissue 21 and a section of inferior colon tissue 22. It is desired to use the surgical stapling instrument 25 to join these tissue portions 20, 21 together in an end to end anastomosis. As shown in FIG. 3, the stapling head assembly 40 of the surgical stapling instrument 25 has been inserted into the rectum (not shown) and is positioned just inside the severed end of the inferior colon tissue 21. The dome-like anvil shroud 64 of the anvil assembly 60 facilitates the passage of the stapling end effector 37 through the inferior colon tissue 21 without inducing trauma. The anvil assembly 60 is extended and is shown placed just inside the superior colon tissue 22. Anvil assembly 60 is removeably attached to the trocar 43 by the trocar clips 65 described previously. The staples 55 are shown positioned within the staple slots 52.

In FIG. 4, a purse string suture 26 (FIG. 4) is placed adjacent to the severed ends of the tissue in both the inferior colon tissue 21 and the superior colon tissue 22. The ends of the purse string sutures 26 are drawn tight to draw the colon tissue 21, 22 inward about the anvil shaft 62 and the trocar 43. The purse string sutures 26 are then tied to secure the tissue colon tissue 21, 22 in the position shown.

In FIG. 5, the anvil assembly 60 has moved from the open position of FIG. 4 to a closed position adjacent to the stapling head assembly 40 by the clockwise rotation of the anvil closure knob 31 (FIG. 1). As the anvil assembly 60 is closed, the trocar 43 and the anvil shaft 62 are retracted into the central support tube 42 of the stapling head assembly 40 and through the tied ends of the inferior colon tissue 21 and the superior colon tissue 22. Colon tissue 21, 22 is clamped between the stapling head 40 and the anvil assembly 60. The operator continues to close the anvil assembly 60 until a desired gap "D" between the anvil assembly 60 and the staple holder 50 of the stapling head assembly 40 is obtained. The gap "D" sets the height or amount of closure that the staples 55 will undergo when fired. Once the desired gap "D" is reached, the surgical stapling instrument 25 is ready to fire.

Figure 6:
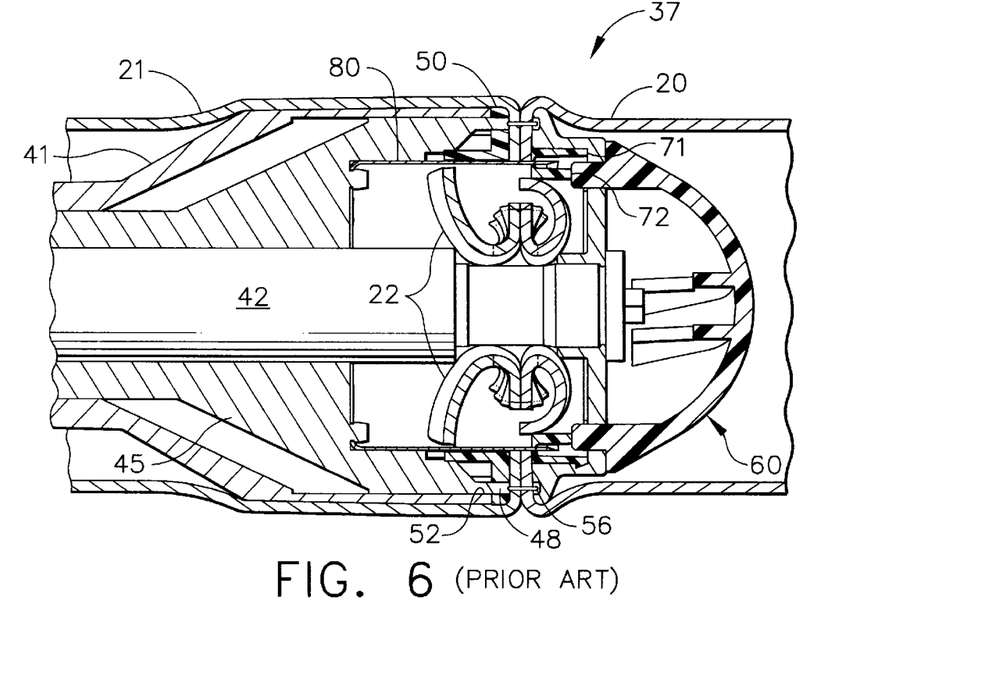
FIG. 6 is a side elevational view, in cross section, of FIG. 6 wherein the surgical anastomosis stapling instrument has been fired to staple the colon tissue together and sever the drawn colon tissue.
Figure 7:
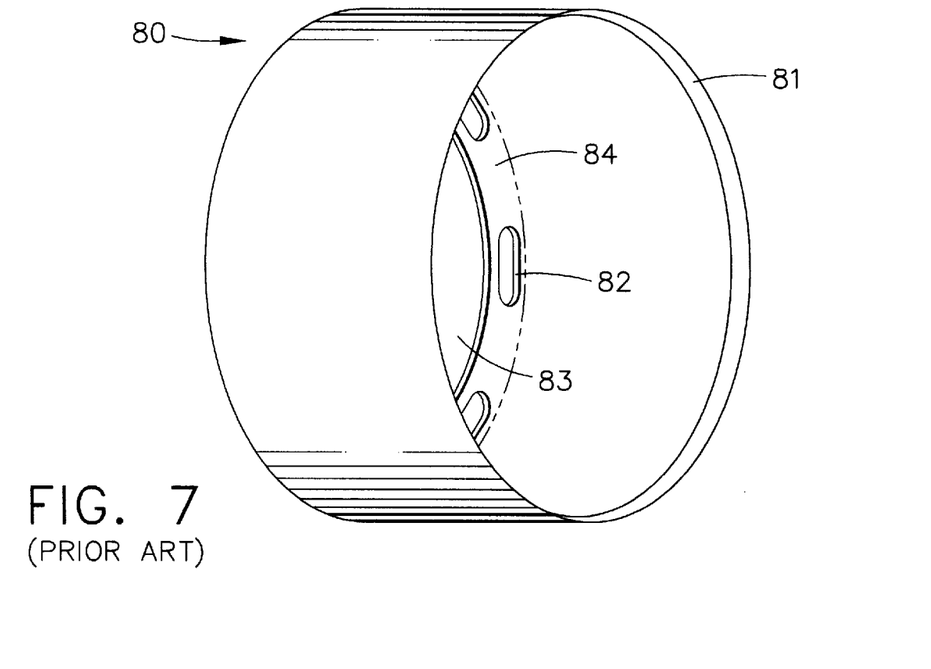
FIG. 7 is an isometric view of the prior art circular blade of the surgical anastomosis stapling instrument of FIG. 1.

In FIG. 6, the surgical stapling instrument 25 of FIG. 5 has been fired. This is accomplished by pivoting the safety latch 33 (FIG. 1) downward (not shown) to unlock the firing trigger 32 and firing the surgical stapling instrument 25 by moving the firing trigger 32 from a first open position (FIG. 1) to a second closed position (not shown) adjacent to the handle 30. Firing the surgical stapling instrument 25 moves the staple driver 45 distally and the driver fingers 48 of the staple driver 45 eject the unformed staples 55 from the staple slots 52. The ejected staples 55 are driven into the inferior colon tissue 21, the superior colon tissue 22, and into the staple forming pockets 63. This action forms the unformed staples 55 into the B-shaped configuration known as a formed staple 56 to join the inferior colon section 21 to the superior colon section 22.

As the staple driver 45 is advanced to form the staples 55, the attached prior art circular blade 80 (see FIG. 7) moves distally to sever the colon tissue 21, 22 against the breakaway washer 70 and produces a portion of severed tissue 22 held within the blade 80. As the staple driver 45 continues to advance to complete the firing stroke, the entire annular cutting edge 81 of the prior art circular blade 80 simultaneously contacts the annular thin web 73 of the breakaway washer 70 (FIG. 6). As the cutting edge 81 continues to advance, the load or force to fire rises to a maximum until the cutting edge 81 simultaneously severs or punches through the entire thin web 73 of the breakaway washer 70.

The severing of the thin web 73 of the breakaway washer results in an abrupt drop in the force to fire and provides both a tactile and an audible feedback that is appreciated by many surgeons as it indicates that the firing of the instrument is complete.

Figure 13:
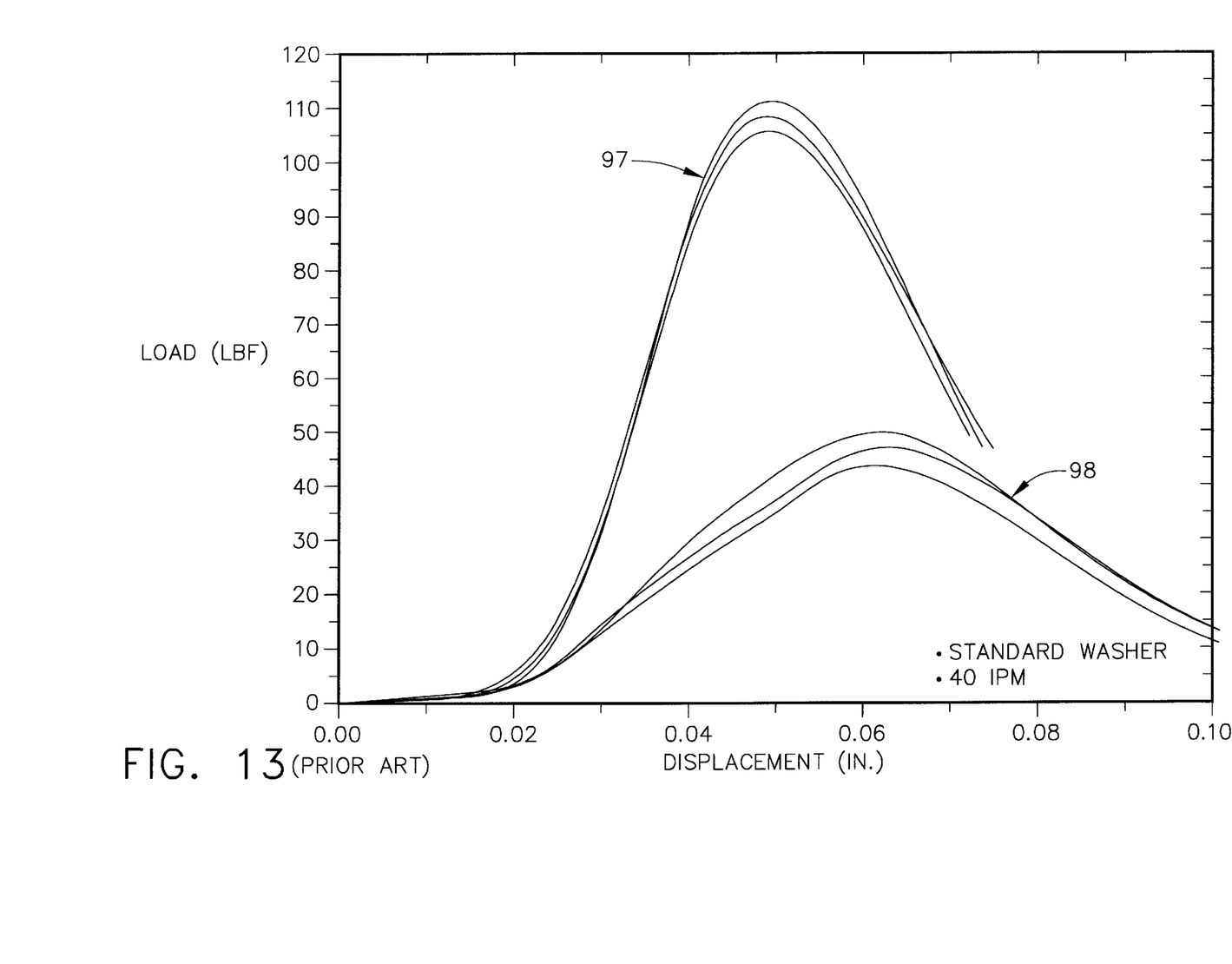
FIG. 13 is a graph showing three examples of the prior art circular blade load/displacement curve and three examples of the prior art circular blade load having undulating cutting edge displacement curves.

In FIG. 13, two sets of load versus displacement curves are shown in a graph format. The curves were generated upon a load/displacement measurement device (not shown) such as the Instron model number 4204 made by Instron of Canton, Mass. All tests were performed using a standard breakaway washer 70 fixed to the base of the Instron with a circular blade attached to the moveable crosshead of the Instron. The moveable crosshead was configured to run at a speed of 40 inches per minute and to travel a total distance of 0.10 inches to sever the web 73 of the breakaway washer 70 with the circular blade. Three tests were run using the prior art circular blade 80 of FIG. 7 against the standard breakaway washer 70 and the results were recorded as a number of prior art load/displacement curves 97 of FIG. 13. The x-axis of the graph of FIG. 13 represents the displacement of the circular blade and the y-axis represents the load (LBF or pound-force) applied to the circular blade. Testing has shown that the force or load required to penetrate the breakaway washer 70 with the prior art blade 80 is a large portion of the firing force.

Figure 8:
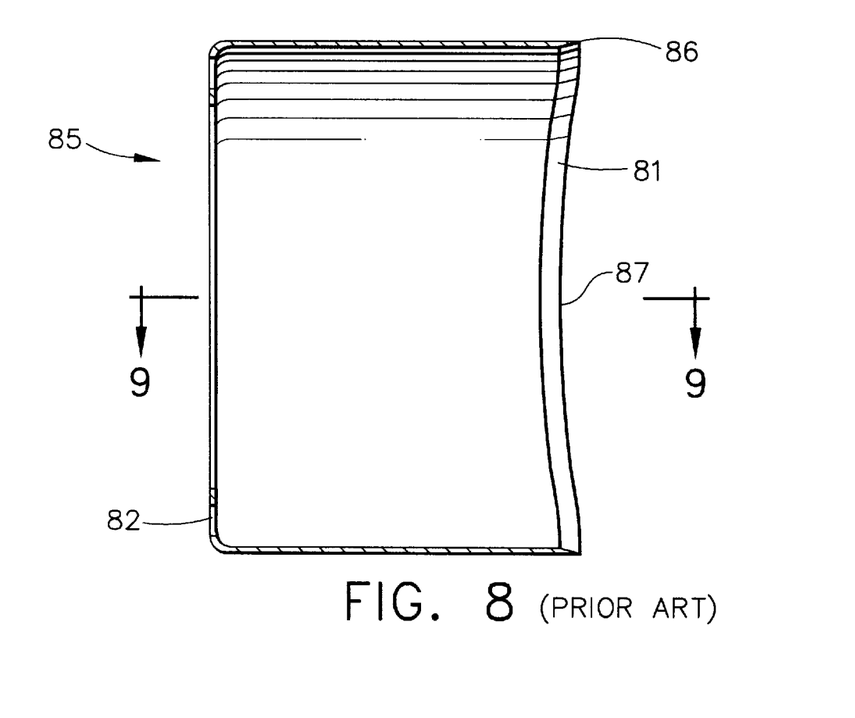
FIG. 8 is a side elevational view, in cross section, of prior art circular blade having an undulated cutting edge for the surgical anastomosis stapling instrument of FIG. 1.
Figure 9:
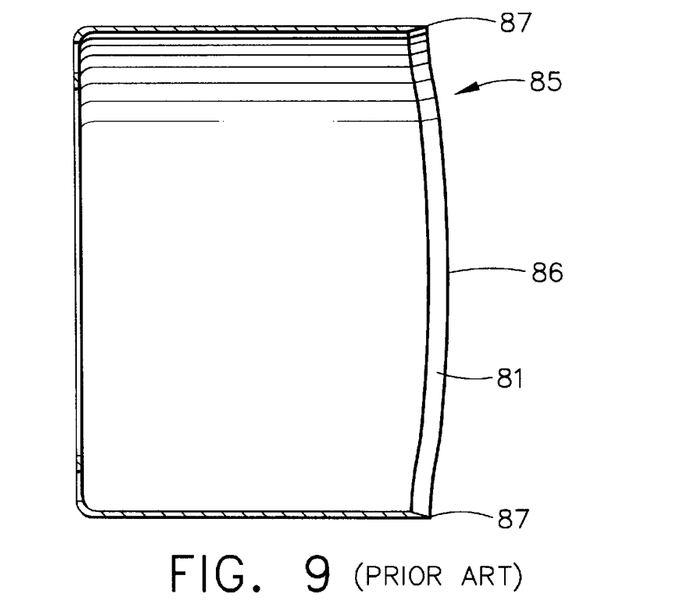
FIG. 9 is a side elevational view, taken in cross section along the line 9—9 of the prior art circular blade of FIG. 8.

Three additional tests were run using a prior art undulating circular blade 85 of FIGS. 8 and 9 against the standard breakaway washer 70 and these results were likewise recorded as the improved circular blade load/displacement curves 98 (FIG. 13). The undulating circular blade 85 is similar to the blade taught in U.S. Pat. No. 4,289,133 by Robert Rothfus, which is included herein by reference, but has a fewer number of peaks 86 and valleys 87 than Rothfus. As anticipated by Rothfus, the undulating circular blade 85 did indeed reduce the peak force to sever the thin web 80 and this is shown in a number of undulating blade load/displacement curves 86 in FIG. 13.

When the prior art circular blade 80 load/displacement curves 97 are compared to the undulating circular blade 85 load/displacement curves 98, the circular blade load/displacement curves 98 show that the maximum peak load is reduced from approximately 112 LBF to approximately 49 LBF. This reduction in peak loading is accomplished by spreading the load out over more of the blade travel or blade displacement, e.g. firing trigger 32 closure and by slicing the thin web 73 of the breakaway washer 70 rather than severing or punching it. It is important to note, however, that although the undulating circular blade 85 has a significant reduction in force to fire, the surgeon loses the andible and tactile feedback provided by the circular blade 80.

Figure 10:
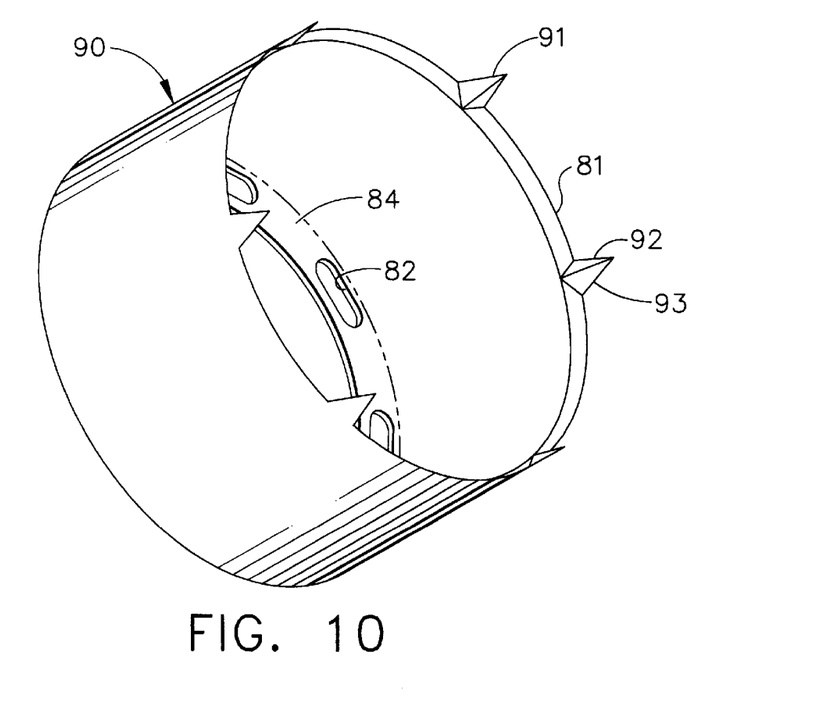
FIG. 10 is an isometric view of an improved circular blade having a plurality of wedge spikes according to the present invention.
Figure 14:
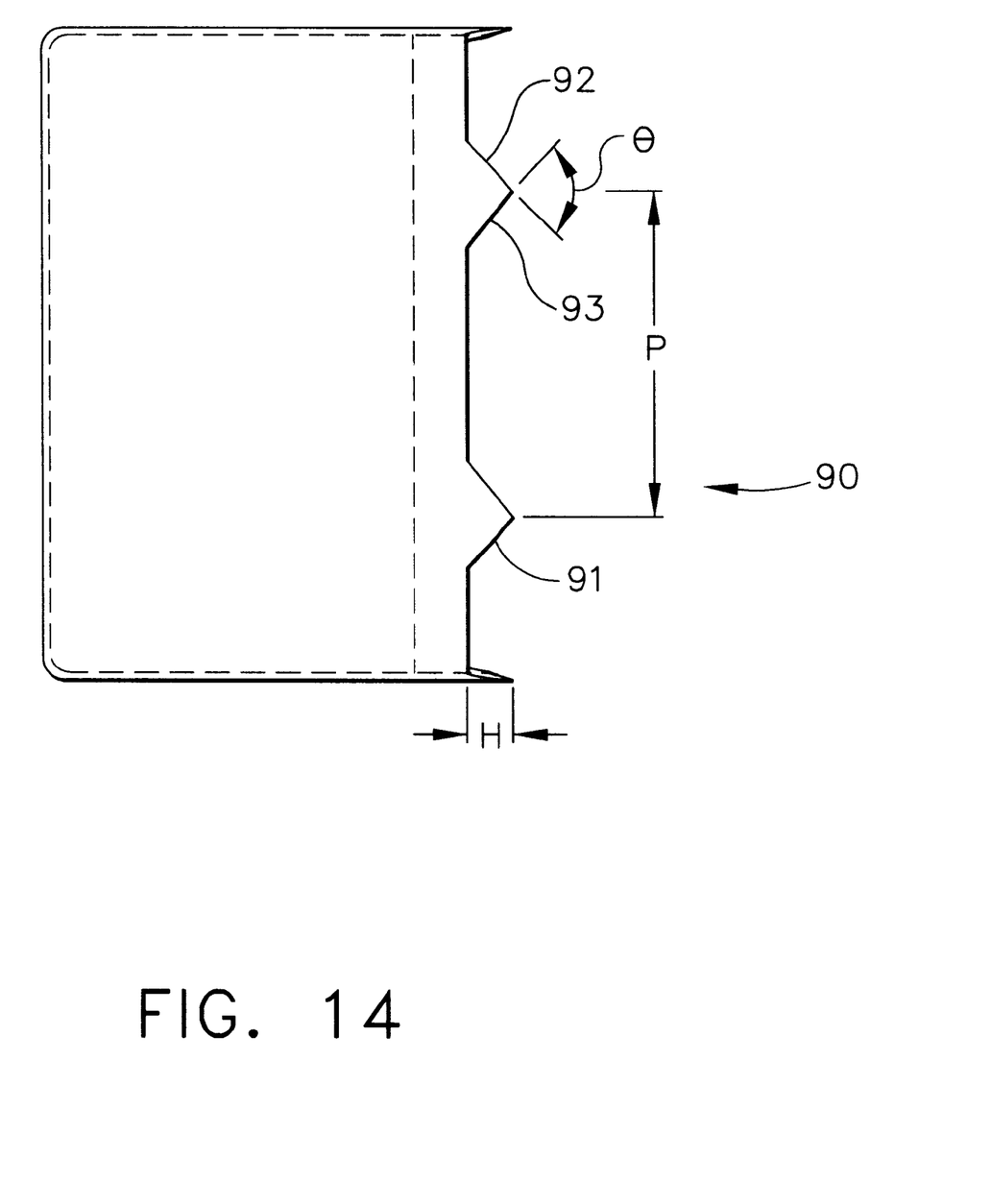
FIG. 14 is a side elevational view of FIG. 10.

In FIG. 10, the spiked circular blade 90 of the preferred invention is shown. The spiked circular blade 90 has a plurality of wedge spikes 91 extending distally from the distal cutting edge 81. The wedge spikes 91 have a first edge 92 and a second edge 93. The spiked circular blade 90 is a generally a hollow cylinder having a proximal blade base 84, a central aperture 83 and a series of blade mounting holes 82 equally spaced around the blade base 84. The cutting edge 81 of the spiked circular blade 90 is formed parallel to the blade base 84 in the manner of the prior art blade 80. The spiked circular blade 90 is designed to mount within and attaches to the staple driver 45 in the manner of the prior art circular blade 80 described above. FIG. 14 further defines the spiked blade 90 of the present invention. As shown, the spiked circular blade 90 has a number of wedge spikes 91 equally spaced at a pitch or spacing "P" about the cutting edge 81. A wedge angle θ exists between the first edge 92 and the second edge 93 of the wedge spike 91. Preferably, angle θ ranges between about 5 degrees and about 120 degrees, and most preferably angle θ is about 15 degrees. The height of the wedge spike 91 from the cutting edge 81 is a dimension "H" that preferably ranges between about 0.020 inches to about 0.25 inches, and most preferably, is about 0.050 inches. Care must be taken to use appropriate values of "P", "θ", and "H" so that the cracks propagated by the wedge spikes 91 do not totally sever the thin web 73 of the breakaway washer 70. The advantages of the spiked circular blade 90 will now be described.

Unlike the prior art blades 80 and 85, the spiked blade 90 according to the present invention severs the breakaway washer 70 in a two step process. The first step is to partially weaken the thin web 73 of the breakaway washer 70 with the wedge spikes 91 of the spiked circular blade 90. The second step is the severing of the partially weakened breakaway washer 70 with the cutting edge 81 in the manner of the prior art blade 80 described above. This two step cutting action both reduces the force or load needed to sever the breakaway washer 70 and provides the tactile and audible feedback that is appreciated by many surgeons.

Figure 11:
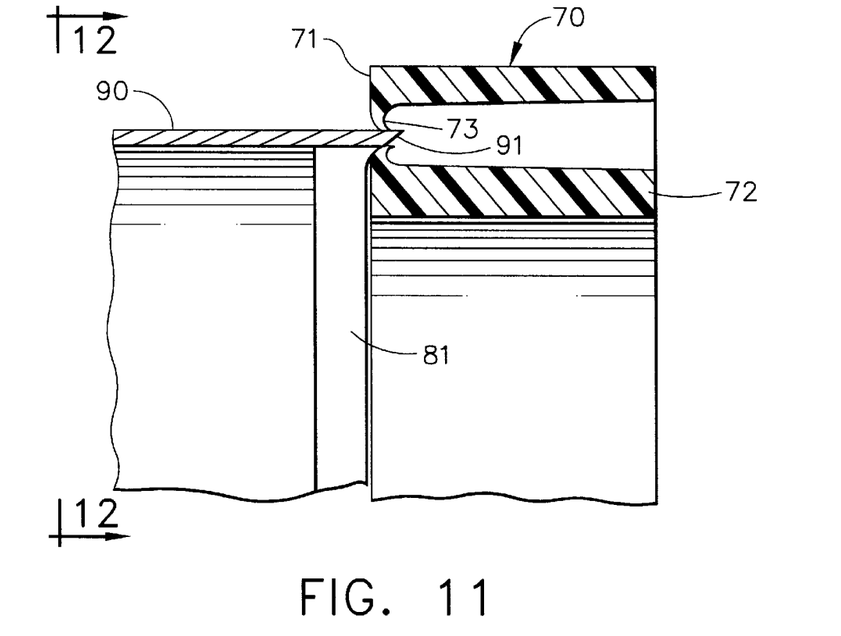
FIG. 11 is a portion of a side elevational view, taken in cross section, of the improved circular blade of FIG. 10 in contact with a breakaway washer.
Figure 12:
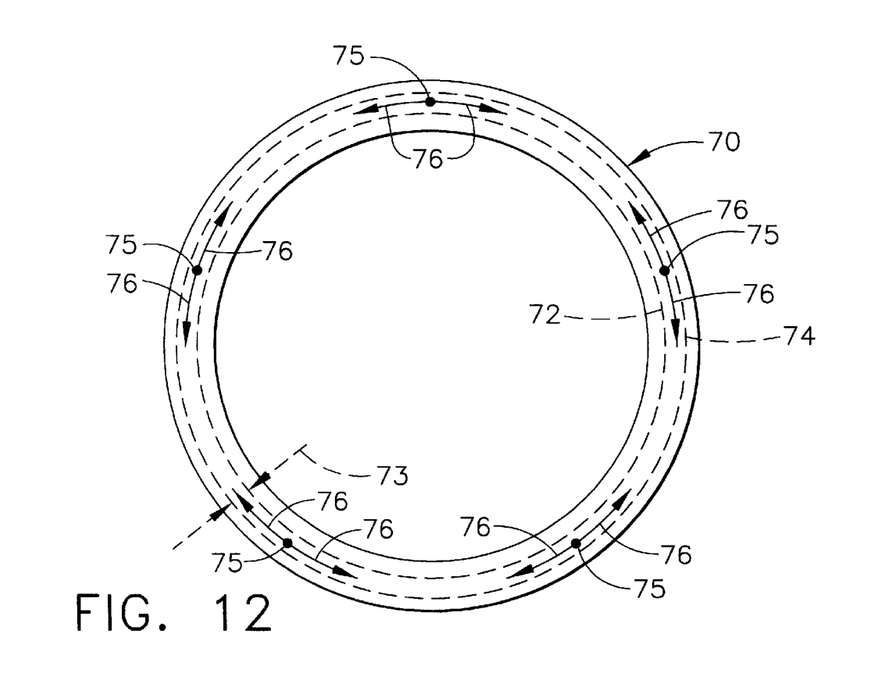
FIG. 12 is a plan view of the cutting surface of the breakaway washer of FIG. 11 showing the points of penetration and cracks propagating therefrom for the improved circular blade.

FIGS. 11 and 12 illustrate the results of the first step of partially weakening the breakaway washer 70. In FIG. 12, a front plan view of the breakaway washer 70 is shown and the spiked circular blade 90 has been removed for clarity. In these figures, the wedge spikes 91 have penetrated the thin web 73 of the breakaway washer 70 at a point of penetration 75. The wedge spikes 91 use wedging action to induce a large stress within the thin web 73 of the breakaway washer, that is concentrated at the point of penetration 75. The localized stress cracks the thin web 73 adjacent to the wedge spikes 91 and a crack 76 propagates away from the point of penetration 73 along the curve of the thin web 73. These cracks 76 weaken the thin web 73 of the breakaway washer 70 without severing it and arrowheads are provided to indicate the direction of crack propagation away from the points of penetration 75.

As the spiked circular blade 90 continues to advance distally from the position of FIG. 11, the blade edge 81 contacts and severs the weakened thin web 73 of the breakaway washer in the manner described above for the prior art blade 80 (not shown). Pre-cracking the breakaway washer 70 provides less material for the cutting edge 81 to sever and the load or force required to sever the cracked thin web 73 of the breakaway washer 70 is reduced by an amount equivalent to the percentage of thin web 73 breakage. Additionally, once a crack is started in a material, the high stress concentrations present at the tip of a crack 76 require less of a load input to propagate the crack farther when subjected to an additional moderate load. The application of the second step of applying the severing load or force to the thin web 73 can induce additional crack propagation resulting in an additional reduction in the force to shear the breakaway washer 70. Thus, the spiked circular blade 90 provides the surgeon with the desired audible and tactile indicators along with a reduced peak force.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical cutting and stapling and instrument for applying a plurality of staples to tissue, said surgical stapling instrument comprising:
   a handle portion;
   a firing trigger pivotably connected to said handle portion;
   a shaft extending from said handle portion;
   a stapling head attached to said shaft and having a distal face, said distal face having an array of staple slots and staples therein, said staples operably coupled to said firing trigger;
   an anvil coupled to said stapling head, said anvil having an array of staple forming pockets therein, said staple forming pockets facing said distal face of said stapling head and in alignment with said staple slots in said distal face for forming said staples therebetween;
   a breakaway washer mounted within said anvil of said stapling head, said breakaway washer having a pair of parallel spaced walls and a thin web extending therebetween, said thin web facing said distal face of said stapling head;
   a blade located within said distal face of said stapling head and operably coupled to said firing trigger, said blade having a distal cutting edge and at least one wedge spike protruding distally therefrom, said at least one wedge spike having a first and a second edge, said distal cutting edge and said at least one wedge spike facing said annular thin web of said breakaway washer; and
   wherein when said anvil is moved adjacent to said stapling head and said firing trigger is closed, said staples are formed and said blade is moved to sever said breakaway washer, and when said blade is moved, said at least one wedge spike of said blade penetrates said thin web of said breakaway washer and weakens said thin web by propagating at least one crack therein, and said distal cutting edge of said blade severs said thin web having at least one crack therein.

2. The instrument of claim 1 wherein said at least one wedge spike has an angle between said first and said second wedge edges between about 5 degrees and about 120 degrees.

3. The instrument of claim 2 wherein said angle between said first and said second wedge edges is preferably about 15 degrees.

4. The instrument of claim 1 wherein said blade is circular.

5. The instrument of claim 1 wherein a distal height of the wedge spike from said cutting edge preferably ranges between about 0.020 inches to about 0.25 inches.

6. The instrument of claim 5 wherein said distal height of said wedge spike from said cutting edge is about 0.050 inches.

7. The instrument of claim 5 wherein said at least one wedge spike has an angle between said first and said second edge between about 5 degrees and about 120 degrees.

8. The instrument of claim 7 wherein said angle between said first and said second edge of said wedge spike is preferably about 15 degrees.

9. A method for stapling and cutting tissue comprising the steps of:
   a) providing a stapling and cutting instrument having:
      i) a handle portion;
      ii) a firing trigger pivotably connected to said handle portion;
      iii) a shaft extending distally from said handle portion;
      iv) a stapling head attached to said shaft and having a distal face, said distal face having an array of staple slots and staples therein, said staples operably coupled to said firing trigger;
      v) an anvil coupled to said stapling head, said anvil having an array of staple forming pockets therein, said staple forming pockets facing said distal face of said stapling head and in alignment with said staple slots in said distal face for forming said staples therebetween;
      vi) a breakaway washer mounted within said anvil of said stapling head, said breakaway washer having a pair of parallel spaced walls and a thin web extending therebetween, said thin web facing said distal face of said stapling head;
      vii) a blade located within said distal face of said stapling head and operably coupled to said firing trigger, said blade having a distal cutting edge and at least one wedge spike protruding distally therefrom, said at least one wedge spike having a first and a second edge, said distal cutting edge and said at least one wedge spike facing said annular thin web of said breakaway washer;
   b) clamping tissue between said anvil assembly and said head assembly;
   c) forming said array of staples against said staple forming pockets;
   d) penetrating the tissue and said thin web of said breakaway washer with said at least one wedge spike to propagate at least one crack within said thin web; and
   e) severing said tissue and said thin web of said breakaway washer having at least one crack therein with said distal cutting edge.

* * * * *